United States Patent [19]
Ohkoshi et al.

[11] Patent Number: 5,684,187
[45] Date of Patent: Nov. 4, 1997

[54] PROCESS FOR PRODUCING HIGHLY PURE TEREPHTHALIC ACID

[75] Inventors: Fumio Ohkoshi; Masato Inary; Fumiya Zaima, all of Kurashiki, Japan

[73] Assignees: Mitsubishi Gas Chemical Co., Inc., Tokyo; Toyo Boseki Kabushiki Kaisha, Osaka; Mizushima Aroma Co., Ltd., Kurashiki, all of Japan

[21] Appl. No.: 639,966

[22] Filed: Apr. 29, 1996

[30] Foreign Application Priority Data

May 17, 1995 [JP] Japan .................................. 7-118299

[51] Int. Cl.$^6$ .................................................. C07C 51/42
[52] U.S. Cl. ........................................ 562/486; 562/485
[58] Field of Search ............................... 562/486, 488

[56] References Cited

U.S. PATENT DOCUMENTS

4,201,871  5/1980  Tanouchi et al. ..................... 562/486

*Primary Examiner*—Samuel Barts
*Attorney, Agent, or Firm*—Frishauf, Holtz, Goodman, Langer & Chick, P.C.

[57] ABSTRACT

There is disclosed a process for producing highly pure terephthalic acid by converting a slurry of terephthalic acid crystals in acetic acid solvent which crystals are obtained by liquid-phase oxidation of p-alkylbenzene, into a slurry thereof in water solvent by mother liquor replacement and then subjecting the latter slurry to a catalytic hydrogenation treatment which process comprises the steps of introducing the slurry of terephthalic acid crystals in acetic acid into a mother liquor replacement column at the top portion; forming an accumulation layer of the terephthalic acid crystals at the bottom portion by the sedimentation of the crystals; feeding replacing water sufficient for the formation of upward rising stream of water to the inside of the column at the bottom portion; and withdrawing the accumulation layer of the crystals from the bottom portion of the column. The accumulation layer is kept at a slightly fluidized stable state and is smoothly withdrawn from the bottom of the column by slowly rotating an arm-type agitation blade placed in the layer or by feeding the replacing water dividedly into two trains.

14 Claims, 3 Drawing Sheets

PROCESS FOR PRODUCING HIGHLY PURE TEREPHTHALIC ACID

BACKGROUND OF THE INVENTION

1. Field of the Invention

The present invention relates to a process for producing highly pure terephthalic acid. More particularly, it pertains to a mother liquor replacing process for replacing, with water, the mother liquor in the slurry of crude terephthalic acid crystals in acetic acid as the solvent which crystals have been produced by liquid-phase oxidation reaction.

2. Description of Related Art

Terephthalic acid is produced by liquid-phase oxidation reaction of a p-phenylene compound such as a p-alkylbenzene typified by p-xylene usually by the use of acetic acid as a solvent (mother liquor) in the presence of a catalyst such as cobalt and manganese, optionally incorporated with an accelerator such as a bromine compound, acetaldehyde or the like.

However, the reaction product through the aforesaid process contains 4-carboxybenzaldehyde (4CBA), p-toluic acid and a variety of coloring impurities and therefore, highly advanced purifying technique is required in order that highly pure terephthalic acid may be obtained.

As processes for purifying crude terephthalic acid produced by liquid-phase oxidation reaction, mention is made of various known processes such as a process in which crude terephthalic acid is dissolved in water as a solvent at a high temperature and pressure and subjected to a catalytic hydrogenation treatment, oxidation treatment, recrystallization treatment or immersion treatment at a high temperature under a slurry condition in which terephthalic acid is partially dissolved.

In particular, a process in which crude terephthalic acid is dissolved in water and subjected to a catalytic hydrogenation treatment at a high temperature and pressure in the presence of a catalyst of a noble metal belonging to the group VIII of the Periodic table has several tens years of history as a large-scale commericial process for producing highly pure terephthalic acid.

However, a lengthy process step is marked as one of the serious problems with the above-mentioned catalytic hydrogenation treatment. That is to say, even if complicated troublesome units such as catalyst recovery and solvent recovery are excluded from the process, the principal process steps are composed of a series of equipment enumerated as at least one stage of oxidation reactor, crude-system consecutive crystallizers in several numbers, a crude-system dryer, a redissolving vessel, catalytic hydrogenation reactor, refining-system consecutive crystallizers in several numbers, a refining-system separating machine and a refining-system dryer.

As primary causes for such lengthy process steps, reference is made to acetic acid, which is used as a solvent in the reaction for producing crude terephthalic acid through oxidation and to water, which is formed by solvent replacement and which is used in the reaction for purification by catalytic hydrogenation treatment.

In carrying out such solvent replacement, it is obliged to completely separate crude terephthalic acid formed by oxidation from acetic acid used as the solvent and then redissolve the acid in water as the new solvent. In the event that the separation of the crude terephthalic acid from acetic acid is incomplete, whereby the crude terephthalic acid to which acetic acid as the solvent is stuck is fed to the catalytic hydrogenation treatment step, it follows that the acetic acid sticking to the crude terephthalic acid is mixed in water as the solvent in the catalytic hydrogenation treatment step and is discharged outside the reaction system, since acetic acid itself is scarcely subjected to chemical change due to catalytic hydrogenation treatment.

The aforesaid fact signifies the outflow and loss of acetic acid of economical value and necessitates the treatment of the acetic acid to make it harmless to the environment, thus increasing the financial burden.

In order to suppress the financial burden, it is necessary to combine a crude-system dryer with a crude-system separator which separates mother liquor from crystal-containing slurry that comes from the oxidation step and thereby almost completely prevent acetic acid from sticking to and accompanying the crude terephthalic acid to be transferred to the catalytic hydrogenation step. Accordingly, the process step in which such a separator and dryer are combined is used in the existing commericial-scale equipment.

The methods most generally used at the present time for separating mother liquor from crystal-containing slurry include the use of a centrifugal separator or rotary vacuum filter, which are widely used also in the case of separating mother liquor from the slurry of crude terephthalic acid crystals.

The centrifugal separator is used for a process in which acetic acid slurry as the starting raw material is introduced into a basket rotating at a high speed to allow separated mother liquor to overflow at the upside thereof, and to direct separated crystals towards the underside. The centrifugal separator, however, suffers the disadvantage that the maintenance and conservation thereof are troublesome because of the restriction on the structure to be durable under high-speed rotation.

In addition, it is impossible to completely separate the mother liquor from the crystals since the rinse of the crude terephthalic crystals can not be readily and easily carried out, thus making it necessary to provide a drying step on the downstream side of the centrifugal separating step to remove the residual acetic acid sticking to the crude terephthalic acid crystals.

The rotary vacuum filter is used for a process in which the crude terephthalic acid crystals stored in the bottom portion of a housing are raised and rotated accompanying the rotation of a filter medium, usually passed through the rinse point and thereafter separated as filter cake.

The above-mentioned vacuum filter, which need not high speed rotation, comparatively facilitates its maintenance and conservation, but as is the case with the centrifugal separator, it is difficult to completely separate by rinse, the mother liquor from the crystals of crude terephthalic acid to which the mother liquor sticks, thereby necessitating the installation of a dryer on the downstream side thereof.

As a method for the separation of the crystals and removal of the mother liquor which takes the place of the centrifugal separation and the rotary vacuum filtering, there is described, in Japanese Patent Publication No. 5410/1958, a method in which the crude terephthalic acid is recrystallized from water to form a slurry, which is passed through a vertical pipe at a high temperature of 165° C. or higher to sediment terephthalic acid crystals by gravity against the slow upward flow of the hot water and wash the mother liquor. This method, in which terephthalic acid crystals are recrystallized from water, followed by the separation of the mother liquor from the crystals at a high temperature (under pressure), is basically a mother liquor replacement method in which the mother liquor in the slurry of terephthalic acid is replaced with a fresh solvent.

Since gravitation is utilized for sedimenting the crystals in the above-mentioned mother liquor replacement method, the method is excellent in that particular power is dispensed with and is attractive for the simplified equipment to be used. Nevertheless, the method is defective in that replacement efficiency of mother liquor is low and besides it is difficult to scale up the experimental results as such to a commercial production plant.

In order to contrive the enhancement of the replacement efficiency, the upward flow of the hot water may be increased, which however, requires a large amount of solvent or water and besides, lowers the sedimentation rate of the crystals, thus causing a large amount of fine crystals to overflow from the top of the vertical pipe.

In order to overcome the above-mentioned defects, there is proposed in Japanese Patent Application Laid-Open No. 53431/1982, a mother liquor replacement method which combines a gravitational sedimentation step of terephthalic acid crystals that is divided with a plurality of horizontal perforated partition plates with a particle transportation step. Such partition plates are provided for the purpose of enhancing the replacement efficiency of mother liquor by preventing the channelling or back mixing of the fluid in the equipment, but the installation of such partition plates in the mother liquor replacement system utilizing gravitational sedimentation which deals with slurry requires much labor for stabilizing the operation against the occurrence of crystals deposit on the partition plates, clogging in the opening, bulking and the like.

There is also proposed in Japanese Patent Application Laid-Open No. 160942/1989 (EP 321272), a mother liquor replacement column equipped with a lot of trays that are horizontally partitioned with such structure as dropping terephthalic acid crystals with scraping blades which rotate slowly on the trays. According to a working example which replaced acetic acid solvent (mother liquor) for crude terephthalic acid with water by the use of the aforesaid replacement column, there is attained a high level of replacement efficiency of mother liquor presumed to be not less than 99%. However, the laboratory-scale equipment to which was fed terephthalic acid slurry in a rate of about 1 ton/hour in the above-mentioned example, when being expanded to a commercial scale, must treat the terephthalic acid slurry in an amount about 100 times that of the example. When presumption is made of the size of a mother liquor replacement column coping with the throughput, the column is required to have a cross-sectional area about 100 times that of the example. In more detail, since the settling velocity of terephthalic acid crystals in the replacement column is specified by gravitation and the characteristics of the solvent at a definite value irrespective of the size of said column, the cross-sectional area of the commericial-scale column must be about 100 times that of the example under the condition in which the linear velocity of the rising solvent is constant irrespective of the size of said column. Hence, in order to achieve a replacement efficiency of mother liquor as high as the above-mentioned level, a mother liquor replacement column of a huge size is required.

If the mother liquor in the slurry of crude terephthalic acid crystals in acetic acid as the solvent which crystals are obtained by liquid-phase oxidation reaction can be replaced with water by means of the mother liquor replacement column and the resultant slurry of the crude terephthalic acid in water can be directed to the catalytic hydrogenation treatment unit, it is made possible to dispense with the separator for separating the mother liquor from the slurry coming from the oxidation step as well as the dryer that are used in the process step at the present time.

In this connection, with regard to a series of process flow system in which the mother liquor in the slurry of crude terephthalic acid crystals in acetic acid as the solvent is replaced with water, the resultant slurry of said crystals in water is introduced as such to the catalytic hydrogenation treatment unit, and highly pure terephthalic acid is produced therein, the replacement efficiency of acetic acid as the solvent, the loss of acetic acid and the effluent water treatment load due to the loss are each presumed to be as follows.

TABLE 1

| Replacement efficiency of mother liquor (%) | Loss of acetic acid (kg/t TA) | Effluent water treatment load (kg TOD/t TA) |
| --- | --- | --- |
| 99.0 | 19 | 20 |
| 99.5 | 9 | 10 |
| 99.9 | 2 | 2 | where each of the items is defined as follows.

Replacement efficiency of mother liquor (%) =(a−b)/a× 100
where
  a: amount of acetic acid as mother liquid fed to crude-system separation step
  b: amount of acetic acid mixed in catalytic hydrogenation step Loss of acetic acid: Loss of acetic acid in kg accompanying the production of one (1) ton of terephthalic acid (TA)

Effluent water treatment load: chemical oxygen demand in kg equivalent to the loss of acetic acid accompanying the production of one (1) ton of terephthalic acid (TA).

Nevertheless, there has not yet been completed any method for replacing a mother liquor in a series of commericial scale production of highly pure terephthalic acid, that is, any practical technique which can take the place of the functions of the separator for the mother liquor of crude terephthalic acid and the dryer used in the process system at the present time.

It is a general object of the present invention to accomplish a technique for replacing the mother liquor in the slurry solution of crude terephthalic acid crystals in acetic acid as the solvent which crystals are obtained by liquid-phase oxidation reaction with water; and transferring the resultant aqueous slurry of crude terephthalic acid crystals in water solvent from the accumulation layer as such; to the catalytic hydrogenation treatment unit, thereby realizing the simplification of the process flow system in the production plant of highly pure terephthalic acid, which leads to the curtailment of the investment cost and of the expense relating to the operation of the production plant.

It is difficult to strictly define where to draw a boundary between allowable and unallowable economical damages due to the loss of acetic acid and the accompanying effluent water treatment load, since it must be judged from various economic circumstances surrounding the production plant. In general, however, it is judged to be feasible to put into practice on a commercial scale provided that the replacement efficiency of mother liquor is not lower than 99%. Moreover, it is judged that a replacement efficiency exceeding 99.9% can assure the feasibility. Accordingly, a specific target of the present invention is to establish a process for replacing the mother liquor which is highly effective as compared with the conventional process for replacing the same, and at the same time, attain a replacement efficiency thereof of 99% or more, preferably 99.9% or more.

SUMMARY OF THE INVENTION

Under such circumstances, intensive research was continued for long years by the present inventors in order to surpass the preceding technical concept and progress in prior arts for several tens of years, and overcome the technical troubles involved therein. As a result, is has been found that an enhanced replacement efficiency of the mother liquor as high as 99% or more is achieved with a compact simple apparatus by forming an accumulation layer of terephthalic acid crystals in the bottom portion of a mother liquor replacement column and feeding water at the bottom thereof. The present invention has been accomplished by the above-mentioned finding.

Specifically, the present invention is concerned with a process for producing highly pure terephthalic acid by converting a slurry of terephthalic acid crystals in acetic acid as the solvent which crystals are obtained by liquid-phase oxidation of p-alkylbenzene into a slurry thereof in water as the solvent by means of mother liquor replacement and then subjecting the latter slurry to a catalytic hydrogenation treatment which process comprises the steps of introducing said slurry of terephthalic acid crystals in acetic acid in a mother liquor replacement column at the top portion thereof; forming an accumulation layer of the terephthalic acid crystals at the bottom portion thereof by the sedimentation of said crystals; feeding replacing water sufficient for the formation of upward rising stream of water to the inside of the column at the bottom portion thereof; and withdrawing the accumulation layer of said crystals from the bottom portion of said column.

In addition, investigation was made on the countermeasure against the trouble in that the accumulation layer of the terephthalic acid crystals is lowered in its fluidity as the slurry concentration increases, thereby worsening the workability of withdrawing itself. As a result, it has found that, by installing an agitation shaft (agitation shaft of arm type) having a plurality of arms extending in a horizontal direction, in the accumulation layer of said crystals in the present invention and gently rotating said agitation shaft, or by imparting impulse to the above-mentioned accumulation layer by any of various possible means, a slight fluidity is preserved in said accumulation layer; channelling of the replacing water in the accumulation layer is suppressed; dispersion of the replacing water is improved; and besides the operability of the mother liquor replacement column is drastically improved.

It has also been found that, by feeding replacing water dividedly into two trains, that is, to the inside of the accumulation layer and through withdrawal portion thereof as an other countermeasure against the deterioration of the workability, operability of the mother liquor replacement column is drastically improved; temperature setting per each train of the replacing water is made possible; heat sources at low temperatures can be effectively utilized; energy consumption is curtailed; and it is made possible to contrive the reduction of operational cost.

Designation of symbols (FIG. 1 to 3)
101, 201, 301: Mother liquor replacement column
102, 202, 302: Raw slurry feed pump
103, 203, 303: Raw slurry introduction pipe
104, 204, 304: Mother liquor discharge pipe
a: Upside surface of accumulation layer
b: Accumulation layer of terephthalic acid crystals
(FIG. 1)
105 : Crystal withdrawal screw
106 : Screw guide pipe
107 : Crystal withdrawal port
108 : Motor
109 : Slurry tank
110 : Stirring element
111 : Stirrer with heater
112 : Circulation pump
113 : Slurry withdrawal pump
114 : Water feed pump
(FIG. 2)
205 : Screw conveyor for withdrawing crystal
206 : Guid pipe for screw conveyor
207 : Crystal withdrawal port
208 : Motor
209 : Slurry tank
210 : Agitation blade of arm type
211 : Motor
212 : Circulation pump
213 : Slurry withdrawal pump
214 : Water feed pump
(FIG. 3)
305 : Replacing water flowmeter for first train
306 : Replacing water flowmeter for second train
307 : Slurry withdrawal pipe
308 : Agitation blade of arm type
309 : Motor
310 : Slurry withdrawal pump
311 : Replacing water feed pump

DESCRIPTION OF PREFERRED EMBODIMENT

The slurry of crude terephthalic acid crystals in acetic acid as the solvent to be subjected to the mother liquor replacement is produced by oxidizing a p-phenylene compound such as a p-alkylbenzene, typically p-xylene, usually in the presence of a catalyst comprising a salt of a heavy metal such as cobalt and manganese or such a catalyst further incorporated with an accelerator such as a bromine compound, acetaldehyde or the like. There is used as a solvent, acetic acid containing about 3 to 20% of water. The liquid-phase oxidation is carried out preferably by using molecular oxygen, which is usually air or oxygen at a temperature in the range of usually 170° to 230° C. at a pressure in the range of 10 to 30 atm in at least one stage.

The reaction effluent in the form of slurry which has been subjected to liquid-phase oxidation contains a variety of impurities such as 4CBA, p-toluic acid and catalysts in addition to terephthalic acid crystals. It is introduced into a crystallizer or consecutive crystallizers forming two or more stages, each belonging to crude system, and consecutively cooled to a prescribed temperature to crystallize terephthalic acid which has been dissolved in a solvent.

Thereafter the slurry of crude terephalic acid crystals in acetic acid as the solvent is fed to a mother liquor replacement column, where the slurry is directed to the upward rising stream of water and the oxidation reaction mother liquor together with a small amount of fine terephthalic acid crystals ascend accompanying the above stream of water, whereas most of the terephthalic acid crystals descends towards the bottom of the column.

The terephthalic acid crystals thus sedimented is finally withdrawn at the bottom of the column. In the present invention, there is formed, at the bottom portion of the column, an accumulation layer of terephthalic acid crystals, to which replacing water is fed from the bottom of the column. The accumulation layer at the bottom portion of the column is withdrawn by a publicly known technological means in a continuous or intermittent manner, for example, by means of a screw-type crystal scraping apparatus as will be described hereunder in the working examples.

As a result, each of the terephthalic acid crystals in the accumulation layer moves downward, and upward stream of water existing in the column countercurrently comes in contact with the terephthalic acid crystals. Thus it follows that acetic acid solvent which has been stuck to the surfaces of the crystals and a variety of by-produced impurities due to oxidation reaction that are contained in the acetic acid are efficiently washed and separated.

By the foregoing mechanism and function, an aqueous slurry of terephthalic acid crystals in water solvent almost free from acetic acid solvent is taken out from the bottom portion of the column, and can be transferred, without being subjected to any additional treatment, to a step of producing highly pure terephthalic acid by a publicly known refining procedure, generally by a method in which the aqueous slurry in water solvent is dissolved at a high temperature and pressure and is subjected to a catalytic hydrogenation treatment in the presence of a catalyst comprising a noble metal belonging to the group VIII.

In the following, some description will be given of principal conditions in carrying out the present invention.

The replacement efficiency of mother liquor in the mother liquor replacement column is required to attain at least 99%, preferably at least 99.9%. The principal conditions therefor include the preservation of fluidity in the accumulation layer of terephthalic acid crystals and also an appropriate selection of the length (height) of the accumulation layer as well as of the linear velocity (upward rising linear velocity) of water in the column.

The length of the accumulation layer is determined taking into consideration a plurality of operational parameters such as feed velocity of the slurry solution of terephthalic acid to be fed at the top of the replacement column, feed velocity of water at the bottom of the replacement column and withdrawing velocity of slurry of terephthalic acid from the bottom of the replacement column. In practical operational procedure, however, such length of the accumulation layer is achieved by detecting the interface between the sedimentation zone of the crystals and the accumulation layer in the mother liquor replacement column, that is, the upside surface of the accumulation layer and regulating the withdrawing velocity for terephthalic acid crystals so that the aforesaid interface or the upside surface is maintained at a prescribed level.

The key factor of the present invention resides in that quasi-static upward stream of water is generated in the space among the crystals of the accumulation layer, and washes away the acetic acid as the mother liquor sticking to the crystals. The washing effect is enhanced, and consequently the replacement efficiency of mother liquor is improved with an increase in the length of the accumulation layer and vice versa. Accordingly the accumulation layer is preferably as long as possible, but an excessively long layer must be avoided, since it causes a possibility of blocking due to the static pressure of the terephthalic acid crystals. In order to achieve at least 99% replacement efficiency of mother liquor, which efficiency is represented also as a function of the replacement column diameter, the length of the accumulation layer should be at least one fifth of the replacement column diameter.

For the purpose of higher replacement efficiency, the upward linear velocity of the replacing water to be fed at the bottom of the replacement column turns out to be a factor of importance. It stands for the flow rate of the water rising countercurrently against the terephthalic acid in the accumulation layer, and is defined, for convenience, as the linear velocity in the portion of the accumulation layer.

According to experimental results, the replacement efficiency increases with an increase in the upward linear velocity but, when the upward linear velocity exceeds about 3 m/h, the replacement efficiency suddenly falls. By the term 'linear velocity' as used herein is meant superficial linear velocity, that is, a linear velocity obtained on dividing the flow rate by the total cross-sectional area of the replacement column without subtracting the part of the cross-section occupied by the (slurry of the) terephthalic acid crystals (in the accumulation layer). This phenomenon is presumably ascribed to that the downward movement of the terephthalic acid crystals in the accumulation layer is hindered by the upward stream of the water, thereby causing irregular fluidization. In fact, careful visual observation of the accumulation layer at the time of experiment at 4 m/h linear velocity has proved frequent occurrence of slight channelling accompanied by slightly irregular fluidization in the accumulation layer. On the other hand, the replacement efficiency of the mother liquor is almost independent of the replacement column diameter, different from the length of the accumulation layer.

In the case of designing the mother liquor replacement column, therefore, the lower limit of the upward linear velocity should exceed zero, that is, the upward stream need only be substantially formed, while the upper limit thereof should be 3 m/h.

An upward linear velocity higher than the above-mentioned upper limit brings about not only a decrease in the replacement efficiency but also upward carry-over loss of part of the terephthalic acid crystals without sufficient sedimentation and besides causes an increase in water consumption and also an increase in water concentration in the acetic acid mother liquor to be recovered from the top of the replacement column.

The temperature in the mother liquor replacement column is not specifically limited but should be determined, taking into account several factors relating to the production plant of highly pure terephthalic acid.

As an example, mother liquor replacement at a higher temperature is effective in improving the quality of terephthalic acid to be produced. With regard to the usual production plant of terephthalic acid, most of the terephthalic acid formed by the reaction is already present as crystals at the time when it is introduced in crude-system consecutive crystallizers from an oxidation reactor. By the consecutive temperature lowering in the crystallizers, residual terephthalic acid dissolved in the mother liquor is consecutively crystallized. As a general phenomenon, crystals obtained at a high temperature portion has purity higher than that of crystals obtained at a low temperature portion. It is known in the case of the crystallization of terephthalic acid, that 4CBA existing as an impurity is crystallized as a eutectic mixture with terephthalic acid, and the proportion of the eutectic mixture suddenly increases with lowering in temperature. Other impurities such as p-toluic acid and various coloring substances possess the properties almost the same as those of 4CBA. It is therefore, advantageous to carry out mother liquor replacement at a higher temperature in that the crude terephthalic acid obtained in water slurry is enhanced in purity and that the highly pure terephthalic acid obtained through catalytic hydrogenation treatment is improved in quality.

In addition, since the catalytic hydrogenation treatment reaction is put into practice at a high temperature, that is, at 250° C. or higher, the mother liquor replacement, when being carried out at a lower temperature, leads to a loss of thermal energy. Since the oxidation reaction is performed at around 200° C. in most cases, the implementation of the mother liquor replacement at a temperature much lower than 200° C. results in a loss of thermal energy owing to the necessity for repeated temperature raising and lowering. In view of the foregoing, it is desirable that the mother liquor replacement be put into practice at a temperature as close as possible to the oxidation reaction temperature.

The mother liquor replacement column which is of extremely simple structure and minimized in the number of power-driven parts, facilitates the operation at a high temperature and pressure. However, the replacement operation at a high temperature results in an inevitable increase in terephalic acid dissolved in the mother liquor in acetic acid as the solvent which is discharged from the top of the replacement column. Since the mother liquor is recycled through the system as the solvent in the oxidation reaction, such carry-over of the terephthalic acid does not directly lead to the loss thereof, but does lead to substantial decrease in the productivity of the reactor.

Taking into consideration the above-mentioned various conditions, it is preferable that the temperature in the step of mother liquor replacement be set to a temperature lower than that in the oxidation reaction by at most 120° C., that is, to a temperature in the range of about 80 to 180° C.

The pressure in the replacement column is a pressure for maintaining the temperatures of acetic acid and water at respective prescribed levels, and decision of the temperature in the replacement column automatically decides the lower limit of the pressure therein, which is in the range of 0 to 15 kg/cm$^2$G, approximately.

As described hereinbefore, importance is attached to the preservation of fluidity in the accumulation layer of terephthalic acid crystals in the mother liquor replacement column. The reason for this is that if the accumulation layer formed by the sedimentation of terephthalic acid crystals is brought to a complete consolidation state, the crystals are deprived of the characteristics as slurry, thus making it impossible to withdraw from the replacement column by any of technical means. In order to prevent such complete consolidation, it is necessary to fluidize the accumulation layer of terephthalic acid crystals at all times. In addition, by preserving the fluidity of the accumulation layer, the dispersion of the replacing water fed in the column is promoted and the replacing water is prevented from causing channelling while rising in the accumulation layer of terephthalic acid crystals.

Needless to say, when the fluidity of the accumulation layer is made violent, mass transfer therein is accelerated, thereby lowering refining performance of the replacement column, that is, replacement efficiency. In order that the replacement efficiency of mother liquor may not be unreasonably lowered, it is indispensable to control the fluidity of the accumulation layer to a slight level.

An arm type agitation blade is most effective as a means for imparting slight fluidity to the accumulation layer. Any of various means for imparting pulsation will be effectively employed.

Any of arm-type agiation blade is acceptable, provided that the arm extends horizontally from the agitation shaft. The arm is not specifically limited in the number and shape and any form including straight line, cross and comma or eddy pattern when viewed from above the agitation shaft is acceptable. The number of arm stages is determined by the height of the accumulation layer. The shape of cross-section of the arm is not specifically limited unless it is circle, triangle, rhombus or the like, that is, a shape which requires unreasonably high power in shearing the accumulation layer.

The number of revolutions of the arm-type agitation blade is preferably 0.1 to 20, more preferably 0.5 to 10 r.p.m. The diameter of the arm-type agitation blade is required to be sufficient for fluidizing whole of the accumulation layer of terephthalic acid crystals. The blade diameter in a commericial apparatus is preferably 0.7 to 0.99, more preferably 0.8 to 0.99 times the diameter of the bottom portion of the replacement column.

As a means for imparting pulsation to the accumulation layer, reference is made to a method in which feeding and non-feeding of replacing water are alternately intermittently repeated, a method in which pulsation is imparted thereto with a pulsator located in replacing water feed line, a method in which pulsation is directly imparted thereto with a pulsator located in the accumulation portion of terephthalic acid in the column and like method.

By rotating the above-mentioned arm type agitation blade preferably in a gentle manner, it is made possible to preserve slight fluidity in the accumulation layer, and by imparting pulsation to the accumulation layer by any of the aforestated methods, channelling of the replacing water in the accumulation layer is suppressed, dispersion of the replacing water is improved, and besides the operability of the replacement column is drastically improved.

The sedimented terephthalic acid crystals are taken out from the bottom of the replacement column. In the present invention, there is preferably adopted a method in which replacing water is fed through the bottom of the replacement column dividedly into two trains to the accumulation layer formed in the bottom portion of the column.

The replacing water in the first train is fed at the bottom of the accumulation layer, preferably at the bottom of the accumulation layer beneath arm type agitation blades, passed through the accumulation layer in the column mainly as an upward stream, brought into contact countercurrently with sedimenting terephthalic acid crystals, and discharged along with the mother liquor of the oxidation reaction through the top of the replacement column. It is effective to adopt a mentioned arm-type agitation blade as though it were a sprinkler or a method in which replacing water is fed through a ring header which is installed in the accumulation layer for the purpose of improving the dispersion of the replacing water in the accumulation layer and at the same time preventing the replacing water from causing channelling.

The replacing water in the second train is introduced at the withdrawing portion of the accumulation layer by means of a water jet nozzle, a slurry nozzle or a mixer, and is continuously taken out from the bottom of the replacement column.

The temperature of the replacing water in the first train which functions as upward stream in the replacing column is set to a temperature basically the same as that of the terephthalic acid crystals in slurry form that are fed to the top of the column, but may be set to a lower temperature than the foregoing, in which case, the expense required for heating the replacing water is curtailed.

However, even if an attempt is made to increase the difference in temperature between the replacing water which flows as an upward stream in the replacement column and the slurry of terephthalic acid crystals to be fed at the top of the replacement column, there is a limit in the difference in temperature. A difference in temperature exceeding the limit unfavorably brings about several problems such as deposit of terephthalic acid crystals which is prone to adhere to the inside walls of the replacement column and cause clogging, thus impairing operational safety; and necessity for increasing the diameter of the replacement column because of lowered sedimentation velocity of the terephthalic acid crystals, which leads to an increase in equipment investment cost.

In view of the foregoing, the temperature of the replacing water in the first train is set to a temperature same as or lower than by at most 100° C., the temperature of the slurry of terephthalic acid crystals to be fed at the top of the replacement column.

On the other hand, the replacing water in the second train is used for taking out, in a stable manner, the terephthalic acid crystals in the accumulation layer and need only prevent clogging even when terephthalic acid precipitates as crystals. It is preferable that the temperature thereof be set to a temperature same as or lower than by 5° to 100° C., the temperature of the replacing water in the first train. The division of replacing water into two trains enables temperature setting per each train, effective utilization of heat sources at low temperatures in the process plant, curtailment of energy consumption and the reduction of operational cost.

In the following, the present invention will be described in more detail with reference to working examples, which however, shall not be construed to limit the present invention thereto.

EXAMPLE 1

Figure 1:
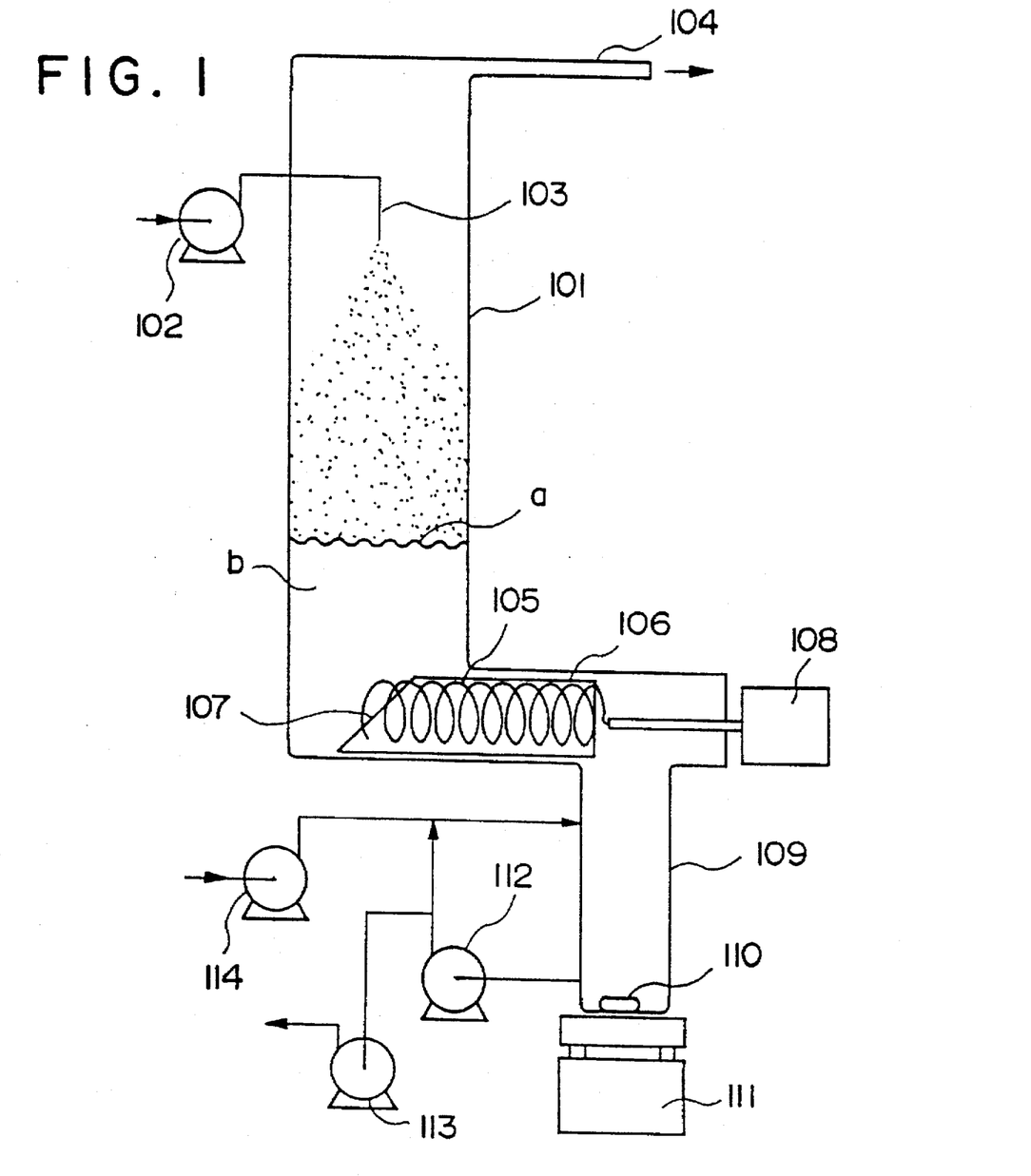
FIG. 1 is an explanatory drawing showing the mother liquor replacement apparatus used in Examples 1 to 19.

There was carried out by using the equipment as illustrated in FIG. 1, an experiment of replacing with water, the mother liquor in the slurry of crude terephthalic acid crystals in acetic acid solvent as the raw slurry which was obtained by liquid-phase oxidation reaction.

In FIG. 1, the mother liquor replacement column 101 is a glass-made cylinder of 36 mm in inside diameter, and equipped with a raw slurry introduction pipe 103 at the top portion thereof, which is connected to a raw slurry feed pump 102; a mother liquor discharge pipe 104 at the top thereof; and a horizontally extended portion at the bottom thereof, which is connected to a slurry tank 109.

The content in the slurry tank 109 is circulated and stirred with a circulation pump 112 which is installed outside the tank. In order to enhance stirring effect, a stirring element 110 is provided at the bottom of the tank and actuated with a stirrer with heater 111 in close contact with the bottom of the tank. A branched pipe to slurry withdrawal pump 113 and a branched pipe to a water feed pump 114 are connected to the return pipe, midway from the circulation pump 112.

The horizontally extended portion at the bottom of the column is equipped inside with a screw guide pipe 106, one end of which reaches the upside end of the slurry tank 109, and the other end of which reaches the middle of the bottom of the column, is cut slantwise and upward, and forms an accumulation layer withdrawal port 107.

The screw guide pipe 106 is equipped inside with a screw of a structure in which stainless steel-made thick wires are spirally wound, one end of which screw reaches the accumulation layer withdrawal port 107, and the other end of which screw reaches the top of the slurry tank 109. The axis of the screw is connected to a motor 108 which is installed outside the column. The portion into which the axis is inserted is sealed with a sealing material made of silicone rubber.

The principal parts of this experimental equipment is composed of a heat resistant glass and is of duplex-pipe structure in whole where possible. The space with annular section between inner and outer pipes is packed in whole with a heat insulating material so that the entire equipment is maintained at the same temperature by circulating an oil the temperature of which is controlled to 92° C. In addition, there are located where necessary, observation ports for visually observing inside of the column.

The ripple-shaped curve "a" as shown horizontally in the middle of the column represents the upside surface of the accumulation layer of terephthalic acid crystals, and the distance between the ripple-shaped curve "a" and the upside end of the screw guide pipe 106 is taken as the length (height) of the accumulation layer.

Water at 92° C. was fed in the reaction system by driving the water feed pump 114. When water began to overflow through the mother liquor discharge pipe 104, the circulation pump 112, slurry withdrawal pump 113 and stirrer with heater 111 were actuated. Then by actuating the raw slurry feed pump 102, raw slurry (crystal concentration of 30%) was fed in the column through the raw slurry introduction pipe 103. There was used, as the raw slurry, a slurry of terephthalic acid in acetic acid solvent. The slurry, which had been produced on a commercial scale, was the reaction product produced by oxidizing p-xylene at 195° C. in a water-containing acetic acid solvent with air blown thereinto in the presence of an oxidation reaction catalyst comprising a cobalt compound, manganese compound and bromine compound. The reaction product was cooled, through three-stage consecutively cooled crystallizers to form a slurry cooled to 80° C., which was again heated to 92° C. and fed to the replacement column 101.

When the height of the accumulation layer reached 20 mm, while the inside of the replacement column was visually observed through the observation ports, the motor 108 was started to rotate the crystal withdrawal screw 105 and start the withdrawal of the crystals.

When the system was brought to a stationary state, the respective flow rates were regulated and set to the following values.

| | |
|---|---|
| Raw slurry feed pump 102 | 2.80 kg/h |
| Slurry withdrawal pump 113 | 2.80 kg/h |
| Water feed pump 114 | 2.84 kg/h |

In this operation, the number of revolutions of the motor 108 was regulated so as to keep 20 mm height of the accumulation layer by visually observing the height at all times. The upward linear velocity of the water in the column under the above-mentioned conditions was about 0.9 m/h.

At the time when continuous running was carried out for 5 hours, samples were collected from each of the specified positions in the experimental equipment and analyzed for chemical composition. The results are as follows:

(1) Mother liquor in the raw slurry (supernatant liquid obtained by cooling the slurry collected with the raw slurry feed pump 102 to room temperature, and allowing the cooled slurry to stand)

| | |
|---|---|
| Acetic acid | 85.2% |
| Water | 14.5% |
| Unknown | 0.3% |

(2) Withdrawn slurry (supernatant liquid obtained by cooling the slurry collected with the slurry withdrawal pump 113 to room temperature, and allowing the cooled slurry to stand)
Acetic acid 0.102%

The replacement efficiency of mother liquor is calculated from these values to be 99.88% based on acetic acid.

EXAMPLE 2

The procedure in Example 1 was repeated to carry out the experiment except that the number of revolutions of the motor 108 was regulated so as to keep 10 mm height of the accumulation layer by visually observing the height at all times. The upward linear velocity of the water in the column under the above-mentioned conditions was about 0.9 m/h, that is, the same as in Example 1.

At the time when continuous running was carried out for 5 hours, samples were collected from each of the specified positions in the experimental equipment and analyzed for chemical composition. The results are as follows:

(1) Mother liquor in the raw slurry (supernatant liquid obtained by cooling the slurry collected with the raw slurry feed pump 102 to room temperature, and allowing the cooled slurry to stand)

| | |
|---|---|
| Acetic acid | 86.1% |
| Water | 13.5% |
| Unknown | 0.4% |

(2) Withdrawn slurry (supernatant liquid obtained by cooling the slurry collected with the slurry withdrawal pump 113 to room temperature, and allowing the cooled slurry to stand)
Acetic acid 0.68%

The replacement efficiency of mother liquor is calculated from these values to be 99.21% based on acetic acid.

EXAMPLE 3 to 19

The procedure in Example 1 was repeated to carry out the experiment except that a mother liquor replacement column of 70 mm in inside diameter was used in Examples 4 to 6 and that of 105 mm in inside diameter was used in Examples 7 to 9 and Examples 15 to 19 and that operational conditions including the accumulation layer length, flow rates of pumps 102, 113 and 114 and upward linear velocity of water were altered in part as given in Table 2. However, the temperature of the replacing treatment was 92° C. for all the examples, that is, the same as that in Example 1.

The replacement efficiency of mother liquor is given in Table 2 together with the operational conditions.

TABLE 2

| | Replacement Column diameter (mm) | Accumulation layer length (mm) | Flow rate Pump 102 (kg/h) | Flow rate Pump 113 (kg/h) | Flow rate Pump 114 (kg/h) | Upward linear velocity (m/h) | Replacement efficiency of mother liquor (%) |
|---|---|---|---|---|---|---|---|
| Example 1 | 36 | 20 | 2.80 | 2.80 | 2.84 | 0.9 | 99.88 |
| Example 2 | 36 | 10 | 2.80 | 2.80 | 2.84 | 0.9 | 99.21 |
| Example 3 | 36 | 5 | 2.80 | 2.80 | 2.84 | 0.9 | 98.74 |
| Example 4 | 70 | 30 | 10.6 | 10.6 | 10.7 | 0.9 | 99.94 |
| Example 5 | 70 | 20 | 10.6 | 10.6 | 10.7 | 0.9 | 99.24 |
| Example 6 | 70 | 10 | 10.6 | 10.6 | 10.7 | 0.9 | 98.92 |
| Example 7 | 105 | 30 | 23.8 | 23.8 | 24.2 | 0.9 | 99.91 |
| Example 8 | 105 | 20 | 23.8 | 23.8 | 24.2 | 0.9 | 99.19 |
| Example 9 | 105 | 10 | 23.8 | 23.8 | 24.2 | 0.9 | 98.85 |
| Example 10 | 36 | 20 | 2.80 | 2.80 | 1.96 | 0 | 98.30 |
| Example 11 | 36 | 20 | 2.80 | 2.80 | 2.45 | 0.5 | 99.56 |
| Example 12 | 36 | 20 | 2.80 | 2.80 | 3.92 | 2.0 | 99.96 |
| Example 13 | 36 | 20 | 2.80 | 2.80 | 4.90 | 3.0 | 99.90 |
| Example 14 | 36 | 20 | 2.80 | 2.80 | 5.88 | 4.0 | 97.03 |
| Example 15 | 105 | 30 | 23.8 | 23.8 | 16.7 | 0 | 97.92 |
| Example 16 | 105 | 30 | 23.8 | 23.8 | 20.8 | 0.5 | 99.63 |
| Example 17 | 105 | 30 | 23.8 | 23.8 | 33.4 | 2.0 | 99.94 |
| Example 18 | 105 | 30 | 23.8 | 23.8 | 41.7 | 3.0 | 99.94 |
| Example 19 | 105 | 30 | 23.8 | 23.8 | 50.1 | 4.0 | 98.12 |

The following conclusion is obtained from the above-described examples.

(1) The replacement efficiency of mother liquor tends to increase with an increase in the length of the accumulation layer (refer to Examples 1 to 3, 4 to 6 and 7 to 9) and tends to decrease with an increase in the inside diameter of the mother liquor replacement column. Hence, in order to keep the replacement efficiency constant, the length of the accumulation layer must be increased with an increase in the inside diameter of the replacement column. Also, in order to achieve a replacement efficiency of at least 99.0% at an upward linear velocity of 0.9 m/h, it is preferable that the length of the accumulation layer be set to at least one fifth the inside diameter of the replacement column.

(2) The replacement efficiency of mother liquor increases with an increase in the upward linear velocity (refer to Examples 10 to 13 and 15 to 18), but tends to decrease therewith when the upward linear velocity exceeds 3 m/hr (refer to Examples 14 and 19). When the replacement efficiency decreased in this way, slight channelling frequently took place in the accumulation layer and slight fluidity of crystals was observed therein. It is thought that the replacement efficiency is independent of the inside diameter of the replacement column when the upward linear velocity is constant.

EXAMPLE 20

Figure 2:
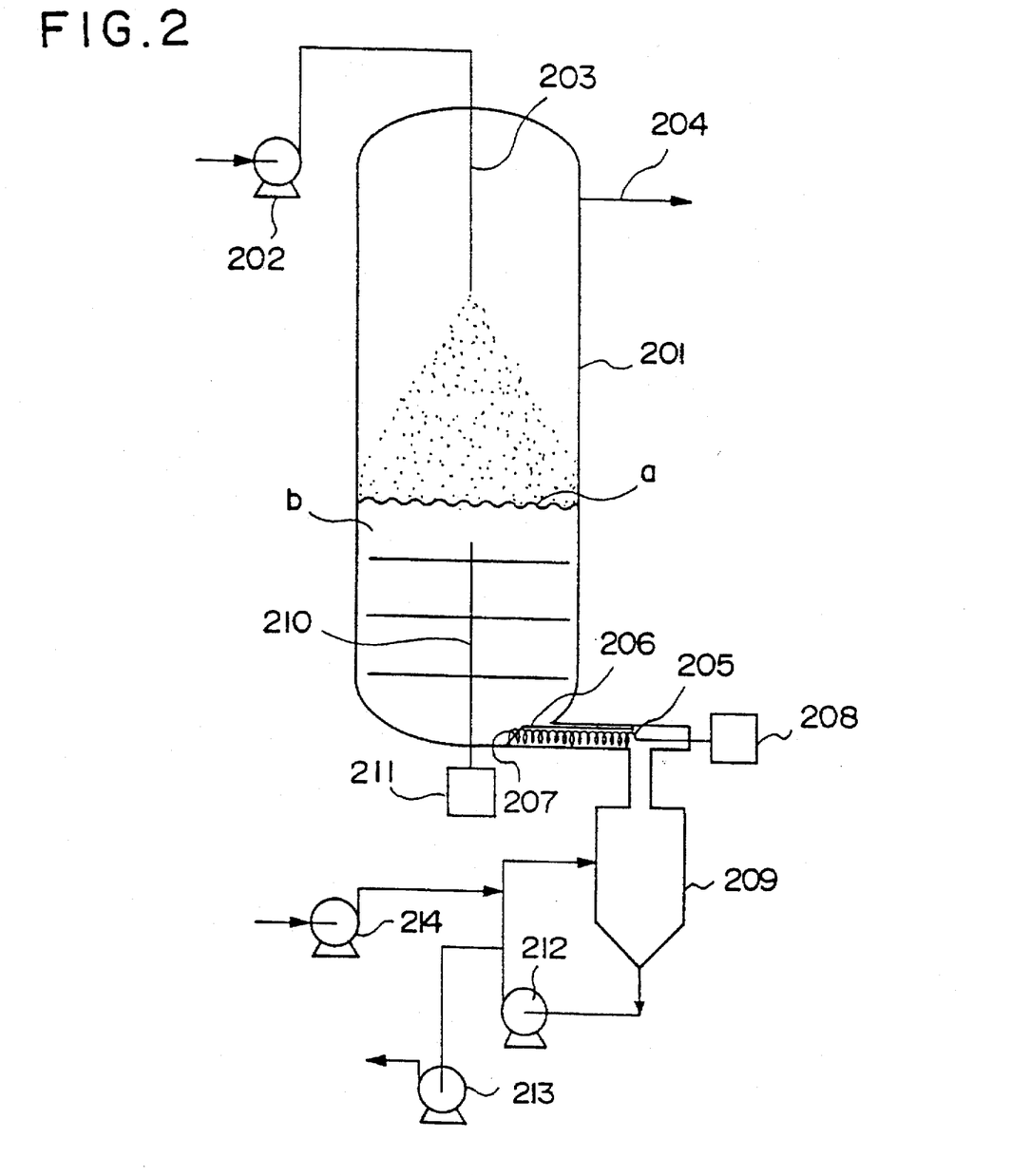
FIG. 2 is an explanatory drawing showing the mother liquor replacement apparatus used in Example 20.

There was carried out by using the equipment as illustrated in FIG. 2, an experiment of replacing with water, the mother liquor in the slurry of crude terephthalic acid crystals in acetic acid solvent as the raw slurry which was obtained by liquid-phase oxidation reaction.

In FIG. 2, the mother liquor replacement column 201 is a stainless steel-made vessel and equipped with a raw slurry introduction pipe 203 at the top portion thereof, which is connected to a raw slurry feed pump 202; and a mother liquor discharge pipe 204 at the top thereof. The bottom of the column is of the structure of half-ellipsoidal dished end, and is connected to a slurry tank 209.

The content in the slurry tank 209 is circulated and stirred with a circulation pump 212 which is installed outside the tank. A branched pipe to a slurry withdrawal pump 213 and a branched pipe to a water feed pump 214 are connected to return pipe, midway from the circulation pump 212.

The bottom of the column is equipped inside with a screw guide pipe 206, one end of which is cut slantwise and upward, and forms an accumulation layer withdrawal port 207.

The screw guide pipe 206 is equipped inside with a screw conveyor, one end of which reaches the accumulation layer withdrawal port 207, and the other end of which reaches the top of the slurry tank 209. The screw conveyor is connected to a motor 208 which is installed outside the column.

The ripple-shaped curve "a" as shown horizontally in the middle of the column represents the upside surface of the accumulation layer of terephthalic acid crystals, and the distance between the ripple-shaped curve "a" and the upside end of the screw guide pipe 206 is taken as the length (height) of the accumulation layer.

Water at 100° C. was fed in the reaction system by driving the water feed pump 214. When water began to overflow through the mother liquor discharge pipe 204, the circulation pump 212, and slurry withdrawal pump 213 were actuated. Then by actuating the motor 211, the arm type agitation blades 210 were rotated at 4 r.p.m. By actuating the raw slurry feed pump 202, raw slurry at 150° C. was fed in the column through the raw slurry introduction pipe 203. There was used, as the raw slurry, a slurry of terephthalic acid in acetic acid solvent. The slurry, which had been produced on a commercial scale, was the reaction product produced by oxidizing p-xylene at 195° C. in a water-containing acetic acid solvent with air blown thereinto in the presence of an oxidation reaction catalyst comprising a cobalt compound, manganese compound and bromine compound. The reaction product was cooled, through several stages consecutively cooled crystallizers to form a slurry cooled to 150° C., which was fed to the replacement column 201.

When the height of the accumulation layer reached the prescribed level, while being detected with a powder level detector, the screw conveyor 205 was rotated by actuating the motor 208 to start the withdrawal of the crystals.

When the system was brought to a stationary state, the respective flow rates were regulated and set to the following values.

| | |
|---|---|
| Raw slurry feed pump 202 | 783 kg/h (crystal concentration of 32.4% by weight) |
| Slurry withdrawal pump 213 | 762 kg/h (crystal concentration of 33.3% by weight) |
| Water feed pump 214 | 586 kg/h |

In this operation, the number of revolutions of the motor 208 was regulated so as to keep a prescribed height of the accumulation layer by monitoring with a powder level detector. The upward linear velocity of the water in the column under the above-mentioned conditions was about 0.88 m/h.

At the time when continuous running was carried out for 3 days, samples were collected from each of the specified positions in the experimental equipment and analyzed for chemical composition. The results are as follows:

(1) Mother liquor in the raw slurry (supernatant liquid obtained by cooling the slurry collected with the raw slurry feed pump 202 to room temperature, and allowing the cooled slurry to stand)

| | |
|---|---|
| Acetic acid | 85.2% |
| Water | 14.5% |
| Unknown | 0.3% |

(2) Withdrawn slurry (supernatant liquid obtained by cooling the slurry collected with the slurry withdrawal pump 213 to room temperature, and allowing the cooled slurry to stand)

| | |
|---|---|
| Acetic acid | 0.102% |

The replacement efficiency of mother liquor is calculated from these values to be 99.9% based on acetic acid.

EXAMPLE 21

Figure 3:
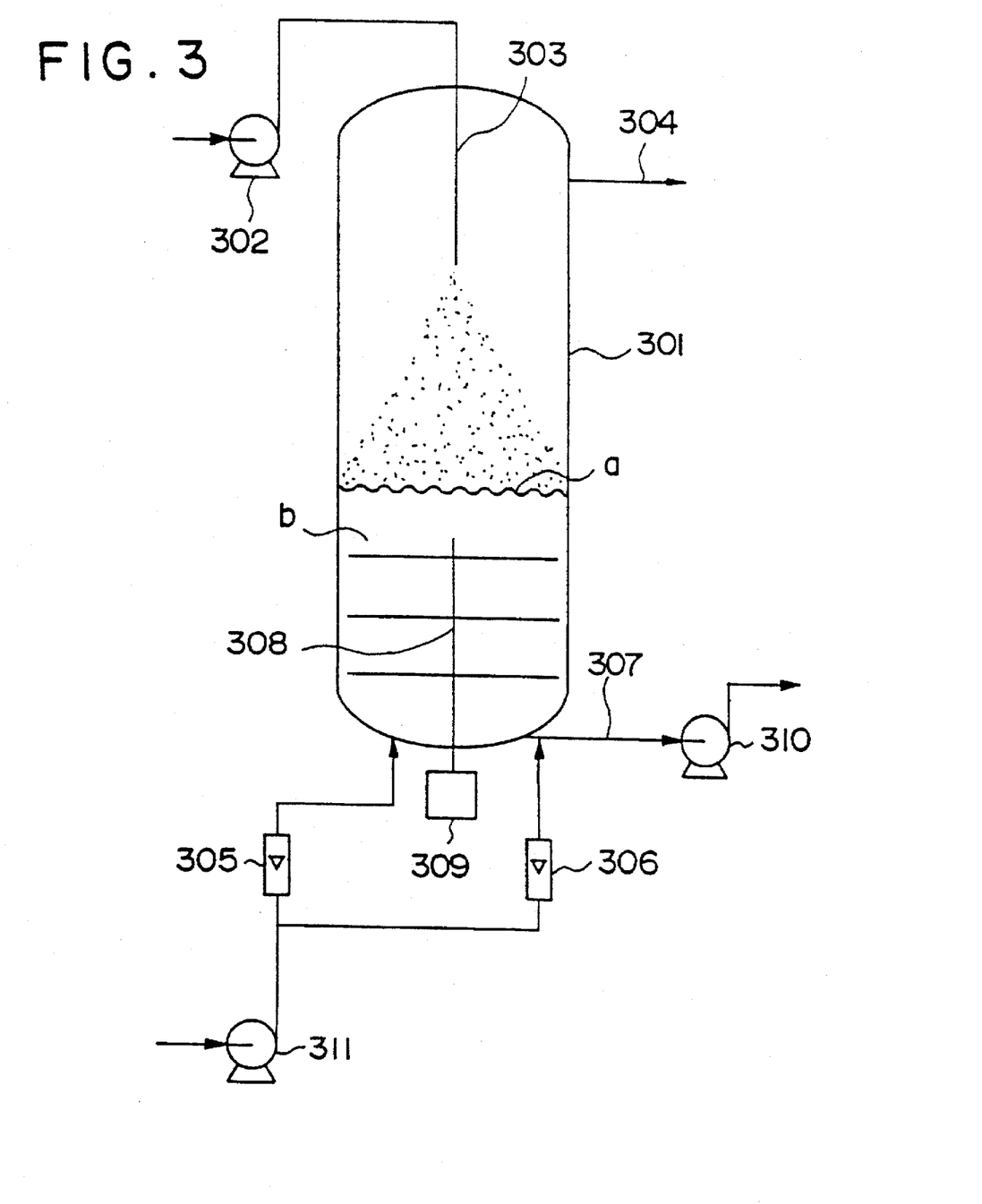
FIG. 3 is an explanatory drawing showing the mother liquor replacement apparatus used in Example 21.

There was carried out by using the equipment as illustrated in FIG. 3, an experiment of replacing with water, the mother liquor in the slurry of crude terephthalic acid crystals in acetic acid solvent as the raw slurry which was obtained by liquid-phase oxidation reaction.

In FIG. 3, the mother liquor replacement column 301 is a stainless steel-made vessel and equipped with a raw slurry introduction pipe 303 at the top portion thereof, which is connected to a raw slurry feed pump 302; and a mother liquor discharge pipe 304 at the top thereof. The bottom of the column is of the structure of half-ellipsoidal dished end, to which are connected, a first-train replacing water introduction pipe through a first-train replacing water flowmeter 305, and a slurry withdrawal pipe 307. To the root of the slurry withdrawal pipe 307, that is, the vicinity of the joint with the bottom of the column, is connected a second-train replacing water introduction pipe through a second-train replacing water flowmeter 306.

The ripple-shaped curve "a" as shown horizontally in the middle of the column represents the upside surface of the accumulation layer of terephthalic acid crystals, and the distance between the ripple-shaped curve "a" and the joint of the slurry withdrawal pipe 307 is taken as the length (height) of the accumulation layer.

Water at 100° C. was fed in the reaction system by driving the water feed pump 311. When water began to overflow through the mother liquor discharge pipe 304, slurry withdrawal pump 310 was actuated. Then by actuating the motor 309, the arm type agitation blades 308 were rotated at 4 r.p.m. By actuating the raw slurry feed pump 302, raw slurry at 150° C. was fed in the column through the raw slurry introduction pipe 303. There was used, as the raw slurry, a slurry of terephthalic acid in acetic acid solvent. The slurry, which had been produced on a commercial scale, was the reaction product produced by oxidizing p-xylene at 195° C. in a water-containing acetic acid solvent with air blown thereinto in the presence of an oxidation reaction catalyst comprising a cobalt compound, manganese compound and bromine compound. The reaction product was cooled, through several stage consecutively cooled crystallizers to form a slurry cooled to 150° C., which was fed to the replacement column 301.

Simultaneously with the feeding of raw slurry at 150° C., the flow rate of the slurry withdrawal pump 310 was adjusted so that the accumulation layer was maintained at a prescribed height, while it was monitored with a powder level detector. The upward linear velocity of the water in the column under these conditions was 0.63 m/h.

When the system was brought to a stationary state, the respective flow rates were regulated and set to the following values.

| | |
|---|---|
| Raw slurry feed pump 302 | 794 kg/h (crystal concentration of 33.1% by weight) |
| Slurry withdrawal pump 310 | 786 kg/h (crystal concentration of 33.5% by weight) |
| Water feed pump 311, first train | 159 kg/h |
| Water feed pump 311, second train | 420 kg/h |

At the time when continuous running was carried out for 3 days, samples were collected from each of the specified positions in the experimental equipment and analyzed for chemical composition. The results are as follows:

(1) Mother liquor in the raw slurry (supernatant liquid obtained by cooling the slurry collected with the raw slurry feed pump 302 to room temperature, and allowing the cooled slurry to stand)

| | |
|---|---|
| Acetic acid | 85.5% |
| Water | 14.1% |
| Unknown | 0.4% |

(2) Withdrawn slurry (supernatant liquid obtained by cooling the slurry collected with the slurry withdrawal pump 310 to room temperature, and allowing the cooled slurry to stand)

| | |
|---|---|
| Acetic acid | 0.099% |

The replacement efficiency of mother liquor is calculated from these values to be 99.9% based on acetic acid.

What is claimed is:

1. A process for producing highly pure terephthalic acid by converting a slurry of terephthalic acid crystals in acetic acid as the solvent which crystals are obtained by liquid-phase oxidation of p-alkylbenzene into a slurry thereof in water as the solvent by means of mother liquor replacement and then subjecting the latter slurry to a catalytic hydrogenation treatment which process comprises the steps of introducing said slurry of terephthalic acid crystals in acetic acid in a mother liquor replacement column at the top portion thereof; forming an accumulation layer of the terephthalic acid crystals at the bottom portion thereof by the sedimentation of said crystals; feeding replacing water sufficient for the formation of upward rising stream of water to the inside of the column at the bottom portion thereof; and withdrawing the accumulation layer of said crystals from the bottom portion of said column.

2. The process for producing highly pure terephthalic acid according to claim 1 wherein the height of the accumulation layer is at least one fifth of the diameter of the mother liquor replacement column.

3. The process for producing highly pure terephthalic acid according to claim 1 wherein the upward stream of water which is formed inside the mother liquor replacement column has a superficial linear velocity of at most 3 m/h based on the accumulation layer of terephthalic acid crystals which is formed in the bottom portion of said column.

4. The process for producing highly pure terephthalic acid according to claim 1 wherein the fluidity in the accumulation layer of terephthalic acid crystals is preserved by the rotation of an arm type agitation blade placed in said accumulation layer.

5. The process for producing highly pure terephthalic acid according to claim 4 wherein the replacing water is fed intermittently.

6. The process for producing highly pure terephthalic acid according to claim 4 wherein the replacing water is fed while being imparted with pulsation.

7. The process for producing highly pure terephthalic acid according to claim 4 wherein the replacing water is fed, while the accumulation layer of terephthalic acid crystals in the bottom portion of the mother liquor replacement column is imparted with pulsation.

8. The process for producing highly pure terephthalic acid according to claim 4 wherein said arm type agitation blade is rotated at a revolution of 0.1 to 20 r.p.m.

9. The process for producing highly pure terephthalic acid according to claim 4 wherein the replacing water is fed through an agitation blade which is placed in the accumulation layer of terephthalic acid crystals.

10. The process for producing highly pure terephthalic acid according to claim 1 wherein the replacing water is fed dividedly to two places including the inside of the accumulation layer of terephthalic acid crystals and a withdrawal portion of said accumulation layer.

11. The process for producing highly pure terephthalic acid according to claim 10 wherein the replacing water is fed to the inside of the accumulation layer through an agitation blade.

12. The process for producing highly pure terephthalic acid according to claim 10 wherein the replacing water is fed to the inside of the accumulation layer through a ring header.

13. The process for producing highly pure terephthalic acid according to claim 10 wherein the temperature of the replacing water fed to the withdrawal portion of said accumulation layer is lower by 5° to 100° C. than the temperature of the replacing water fed to the inside of said accumulation layer.

14. The process for producing highly pure terephthalic acid according to claim 4 wherein the replacing water is fed dividedly to two places including the inside of the accumulation layer of terephthalic acid crystals and a withdrawal portion of said accumulation layer.

* * * * *